United States Patent [19]

Bøgesø et al.

[11] Patent Number: 5,807,855
[45] Date of Patent: Sep. 15, 1998

[54] 1-PIPERAZINO-1,2-DIHYDROINDENE DERIVATIVES

[75] Inventors: Klaus Bøgesø, Hørsholm; Peter Bregnedal, Allerød, both of Denmark

[73] Assignee: H. Lundbeck A/S, Copenhagen-Valby, Denmark

[21] Appl. No.: 331,213

[22] Filed: Oct. 28, 1994

Related U.S. Application Data

[63] Continuation of PCT/DK93/00136 Apr. 23, 1993 published as WO93/22293 Nov. 11, 1993.

[30] Foreign Application Priority Data

Apr. 28, 1992 [DK] Denmark .................................. 0551/92

[51] Int. Cl.$^6$ ....................... A61K 31/495; C07D 241/04; C07D 409/08

[52] U.S. Cl. ......................... 514/252; 514/255; 514/249; 544/231; 544/379; 544/398; 544/401; 544/403; 544/349

[58] Field of Search ..................... 544/231, 379, 544/398, 401, 403; 514/252, 255

[56] References Cited

U.S. PATENT DOCUMENTS

| | | | |
|---|---|---|---|
| 3,996,211 | 12/1976 | Lassen | 260/240 |
| 4,038,395 | 7/1977 | Lassen | 424/250 |
| 4,443,448 | 4/1984 | Bogeso | 514/255 |
| 4,525,360 | 6/1985 | Perregaard | 514/277 |
| 4,684,650 | 8/1987 | Bogeso | 514/252 |
| 4,772,612 | 9/1988 | Goldmann et al. | 514/302 |
| 4,831,031 | 5/1989 | Lowe, III et al. | 514/254 |
| 4,873,344 | 10/1989 | Bogeso et al. | 541/77 |
| 4,946,863 | 8/1990 | Boegesoe et al. | 514/447 |
| 5,643,784 | 7/1997 | Bogeso et al. | 544/285 |

FOREIGN PATENT DOCUMENTS

| | | |
|---|---|---|
| 0 135 781 A1 | 4/1985 | European Pat. Off. . |
| 0 200 322 A1 | 11/1986 | European Pat. Off. . |
| 0 281 309 B1 | 9/1988 | European Pat. Off. . |
| 0 302 423 A3 | 2/1989 | European Pat. Off. . |
| 0 376 607 B1 | 7/1990 | European Pat. Off. . |
| 0 465 398 A2 | 1/1992 | European Pat. Off. . |
| WO91/09594 | 7/1991 | WIPO . |
| WO92/00070 | 1/1992 | WIPO . |
| WO92/10192 | 6/1992 | WIPO . |

OTHER PUBLICATIONS

Barry et al. (1987), "Withdrawal Syndrome Following Subchronic Treatment with Anxiolytic Agents", *Pharmac. Biochem. Behav.*, vol. 27, pp. 239–245.

Bøgesø, K. P. et al. (1985), "3–Phenyl–1–indanamines. Potential Antidepressant Activity and Potent Inhibition of Dopamine, Norepinephrine, and Serotonin Uptake", *J. Med. Chem.*, vol. 28, pp.1817–1828.

Bøgesø, K. P. et al. (1988), "Antihypertensive Activity in a Series of 1–Piperazino–3–phenylindans with Potent 5–HT$_2$ –Antagonostic Activity", *J. Med. Chem.*, vol. 31, pp. 2247–2256.

Bøgesø, K. P. (1983), "Neuroleptic Activity an Dopamine--Uptake Inhibition in 1–Piperazino–3–phenylindans", *J. Med. Chem.*, vol. 26, pp. 935–947.

Hyttel, J. et al. (1985), "Neurochemical Profile of Lu 19–005, a Potent Inhibitor of Uptake of Dopamine, Noradrenaline, and Serotonin", *J. Neurochem.*, vol. 44, pp. 1615–1622.

Sommer, M. B. et al. (1990), "Application of (2–Cyanoaryl) Arylacetonitriles in Cyclization of Annulation Reactions. Preparation of 3–Arylindans, 4–Aryl–3,4–Dihydronaphthalenes, 4–Arylisoquinolines, 1–Aminonaphtalenes, and Heterocyclic Anaolgues", *J. Org. Chem.*, vol. 55, pp. 4822–4827.

Perregaard et al. (1992), "Noncataleptogenic, Centrally Acting Dopamine D–2 and Serotonin 5–HT$_2$ Antagonists within a Series of 3–Substituted 1–(4–Flurophenyl)–1H–Indoles", *J. Med. Chem.*, vol. 35, pp. 1092–1101.

Martin et al. (1989), "Activity of Aromatic Substituted Phenylpiperazines Lacking Affinity for Dopamine Binding Sites in a Preclinical Test of Antipsychotic Efficacy", *J. Med. Chem.*, vol. 32, pp. 1052–1056.

McMillen, B. A. et al. (1988), "N–Alkyl–Substituted Aryl–Piperazine Drugs: Relationship Between Affinity for Serotonin Receptors and Inhabition of Aggression", *Drug Develop. Res.*, vol. 12, pp. 53–62.

(List continued on next page.)

*Primary Examiner*—Emily Bernhardt
*Attorney, Agent, or Firm*—Darby & Darby

[57] ABSTRACT

Trans isomers of 1-piperazino-1,2-dihydroindene compounds having formula (I),

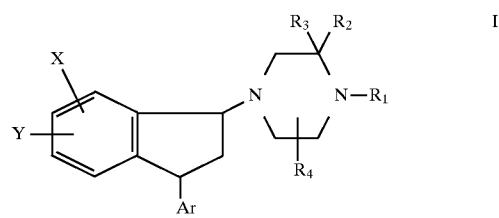

wherein X and Y are hydrogen, halogen, trifluoromethyl, alkyl, alkylthio, trifluoromethylthio, alkoxy, hydroxy, alkylsulfonyl, amino, alkylamino, nitro or cyano; Ar is a phenyl, thienyl or furyl group, each optionally substituted; $R_1$ is hydrogen, or optionally hydroxy substituted alkyl, alkenyl, cycloalkyl or cycloalkylalkyl; $R_2$ is alkyl, alkenyl, cycloalkyl, or cycloalkylalkyl; or $R_1$ and $R_2$ together form a 5 to 7-membered heterocyclic ring fused with the piperazine ring, which ring may be substituted with hydroxy; $R_3$ is hydrogen, alkyl, alkenyl, cycloalkyl or cycloalkylalkyl; or $R_2$ and $R_3$ together form a 3 to 7-membered carbocyclic ring which is spiro-fused to the piperazine ring; and $R_4$ is hydrogen or alkyl. The compounds of the invention have potent antagonist action on dopamine $D_1$ receptors and are useful in the treatment of diseases of the central nervous system, such as psychoses, schizophrenia (positive as well as negative symptoms), anxiety, depression, sleep disturbances, migraine, Parkinson's disease or cocaine abuse.

7 Claims, No Drawings

OTHER PUBLICATIONS

Rao, T. S. et al. (1990), "Inhibition of Climbing and Mossy Fiber, and Basket and Stellate Cell Inputs to Mouse Cerebellar Purkinje Cells by Novel Anti–Ischemic Agents, Ifenprodil and BMY–14802", *Life Sciences*, vol. 47, pp. PL–1–PL–5.

Sanchez et al. (1991), "Neurochemical and In Vivo Pharmacological Profile of Sertindole, a Limbic–Selective, Neuroleptic Compound", *Drug Deve. Res.*, vol. 22, pp. 239–250.

Schwiezer, E. et al. (1986), "Failure of Buspirone to Manage Benzodiazephine Withdrawal", *Am. J. Psychiat.*, vol. 143, No. 12, pp. 1590–1592.

Skarsfeldt, T. et al. (1990), "Sertindole, A New Neuroleptic with Extreme Selectivity on A10 Versus A9 Dopamine Neurones in the Rat", *Eur. J. Pharmacol.*, vol. 182, pp. 613–614.

K. Bøgesø et al. J.Med. Chem., 38 p. 4380 (1995).

P.T. Martin et al., *Schizophrenia Research*, vol. 11, p. 107, (1994).

K. P. Bøgesø et al., *J. Med. Chem.*, vol. 36, pp. 2761–2770, (1993).

J. Hyttel et al., *Clinical Pharm. in Psychiatry*, pp. 109–122, (1989).

J. Arnt et al., *Drug Develop. Res.*, vol. 16, pp. 59–70, (1989).

J. Hyttel et al., *Drug Dev. Res.* 15, 389–404 (1988).

LeFur, G. et al., *Biochem. Parmacol.*, vol. 26, pp. 497–503 (1977).

1-PIPERAZINO-1,2-DIHYDROINDENE DERIVATIVES

This is a continuation of international application Ser. No. PCT/DK93/00136, filed Apr. 23. 1993, published as WO93/22293, Nov. 11, 1993.

The present invention relates to novel 1-piperazino-1,2-dihydroindene derivatives and acid addition salts thereof with activity at dopamine receptors in the central nervous system, in particular potent antagonistic action on dopamine $D_1$ (DA $D_1$) receptors, to medicaments comprising such derivatives as active ingredients, and to the use of such derivatives in the treatment of diseases in the central nervous system.

The novel 1-piperazino-1,2-dihydroindene derivatives of the invention are trans isomers (with respect to the indan ring system) represented by the following Formula I:

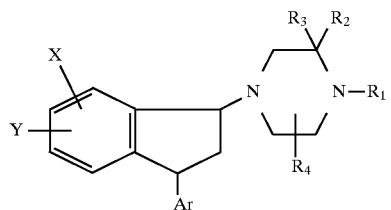

wherein X and Y are independently selected from hydrogen, halogen, trifluoromethyl, lower alkyl, lower alkylthio, trifluoromethylthio, lower alkoxy, hydroxy, lower alkylsulfonyl, amino, lower alkylamino, lower dialkylamino; nitro and cyano;

Ar is a phenyl group, a phenyl group substituted with one or more substituents selected from the group comprising halogen, trifluoromethyl, hydroxy, lower alkoxy and lower alkyl, or Ar is a thienyl group, a furyl group or a thienyl or furyl group substituted with halogen or lower alkyl;

$R_1$ is hydrogen, lower alkyl, lower alkenyl, cycloalkyl or cycloalkylalkyl, each optionally substituted with one or two hydroxy groups;

$R_2$ is lower alkyl, lower alkenyl, cycloalkyl, or cycloalkylalkyl; or $R_1$ and $R_2$ together with the nitrogen and carbon atoms, respectively, to which they are attached form a 5 to 7-membered heterocyclic ring fused with the piperazine ring, which heterocyclic ring may optionally be substituted with hydroxy;

$R_3$ is hydrogen, lower alkyl, lower alkenyl, cycloalkyl or cycloalkylalkyl; or $R_2$ and $R_3$ together with the carbon atom to which they are attached form a 3 to 7-membered carbocyclic ring which is spirofused to the piperazine ring; and $R_4$ is hydrogen or lower alkyl;

provided that $R_2$ and $R_3$ may not form a ring when $R_1$ and $R_2$ together form a ring.

The term "lower alkyl" is intended to mean a straight or branched alkyl group having from one to four carbon atoms, such as methyl, ethyl, n-propyl, iso-propyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

Lower alkenyl is intended to mean an alkenyl group containing from two to four carbon atoms, for example 2-propen-1-yl, 2-buten-1-yl, etc, and cycloalkyl means such a group comprising 3–7 carbon atoms.

Related 1-Piperazino-3-phenylindans being unsubstituted on the piperazine ring carbon atoms and showing potential neuroleptic activity have previously been described in U.S. Pat. No. 4,443,448. Neuroleptic activity was measured as the ability of the compounds to block stereotypies induced by methylphenidate or amphetamine and as the ability to induce catalepsy. Though today regarded as indicating side-effects, catalepsy nevertheless indicate dopaminergic activity. Some of the compounds were also found to show effect as dopamine uptake inhibitors. Later, DA $D_2$ receptor binding data for some of these compounds were reported (K. P. Bøgesø, J. Med. Chem. 1983, 26, 935–947) showing a high affinity for $D_2$ receptors. Furthermore, DA $D_1$ receptor affinity, measured as inhibition of $^3$H-piflutixol binding, of one compound from this series, i.e. tefludazine, has been reported to be substantially lower than the $D_2$ affinity measured as the inhibition of $^3$H-spiperone binding (O. Svendsen et al, Drug. Dev. Res. 1986, 7, 35–47).

Other 1-piperazino-3-phenylindans are disclosed in U.S. Pat. No. 4,684,650. These compounds have been shown to be selective 5-$HT_2$ antagonists, which are inactive or only weakly active as DA antagonists in vivo (methylphenidate antagonism). $D_2$ receptor affinity data for this series were reported by K. P. Bøgesø et al in J. Med. Chem. 1988, 31, 2247–2256 and as expected they had much lower affinity for $D_2$ receptors than for 5-$HT_2$ receptors. The $D_1$ affinity for one compound, irindalone (measured as inhibition of $^3$H-SCH 23390 binding) was even lower than the $D_2$ affinity (Hyttel et al, Drug. Dev. Res. 1988, 15, 389–404).

A profile of mixed DA $D_1/D_2$ receptor inhibition has been observed with some known socalled "atypical" neuroleptic compounds, in particular with clozapine, for which such activities have been shown in animal models measuring effects on $D_1$ and $D_2$ receptors (J. Arnt and J. Hyttel; J. Neural Transmission 1986, 67, 225–240.). Furthermore, ligand binding studies in vitro and in vivo support this observation (J. Hyttel and J. Arnt; Neurobiology of Central $D_1$ dopamine receptors, Plenum Publishing Corporation, 1986. P. H. Andersen; Eur. J. Pharm. 1988, 146, 113–120).

Recently, the mixed occupancy of $D_1$ and $D_2$ receptors by clozapine has been shown by PET scanning experiments in schizophrenic patients (G. Sedvall; TINS 1990, 13, 302–308.). The advantage of mixed $D_1/D_2$ activity is that lower occupancy of each receptor type apparently is necessary in order to control psychosis. For selective $D_2$ antagonists (like haloperidol or perphenazine) higher occupancies of $D_2$ receptors are necessary, but these are accompanied by extrapyramidal side effects (G. Sedvall, 1990, see above).

In addition to $D_1$ and $D_2$ receptor activity, clozapine has also high affinity for 5-$HT_2$ receptors. This effect is at present believed to have a positive influence on the negative symptoms in schizophrenic patients, based upon studies of the 5-$HT_2$ and moderate dopamine receptor antagonist setoperone (Ceulemans et al.; Psychopharmacology 1985, 85, 329–332).

The selective 5-$HT_2$ antagonist ritanserin has been shown to be an antidepressant and to improve depressive symptoms of schizophrenia (E. Klieser, W. H. Strauss; Pharmacopsychiat. 1988, 21, 391–393) and it has been demonstrated to exert effects in an animal test reminiscent of anxiolytic activity (F. C. Colpart et al.; Psychopharmacology 1985, 86, 303–305). Furthermore ritanserin has been shown to improve the quality of sleep (P. A. J. Janssen; Pharmacopsychiat. 1988, 21, 33–37).

Furthermore, animal experiments have indicated that 5-$HT_2$ receptor antagonism might reduce the incidence of extrapyramidal side effects induced by classical neuroleptics (Balsara et al.; Psychopharmacology 1979, 62, 67–69) and ritanserin has been found to relieve neuroleptic-induced parkinsonism (Bersani et al.; Clinical Neuropharmacology, 13, No. 6 (1990), 500–506).

Finally, it is known that 5-HT is involved in migraine attacks. The links between 5-HT and migraine attacks are several and they suggest a number of mechanisms whereby 5-HT may be involved (Scrip Report; "Migraine—Current trends in research and treatment"; PJB Publications Ltd.; May 1991). Various 5-HT$_2$ antagonists are in clinical trials as anti-migraine agents, such as sergolexole (c.f. for example Pharma Projects , May 1991, 1359–1365).

It has been shown (J. Seibyl et al., Abstr. no 148.6, 21st Annual Meeting Society for Neuroscience, New Orleans, Nov. 10–15, 1991) that the DA uptake inhibitor mazindol may be a useful adjunct to standard neuroleptic medication for treating refractory negative symptoms in otherwise stable outpatient schizophrenics.

Furthermore, DA uptake inhibitors may be useful in the treatment of Parkinson's disease, as antidepressant agents or in treatment of cocaine dependence. Possible effect in Parkinson's disease is based on the fact that DA uptake inhibitors are effective in preventing the nigrostriatal toxicity of the neurotoxin MPTP (R. A. Mayer et al., *J. Neurochem*, 1986, 47, 1073–1079), and that MPTP like substances or other neurotoxins utilizing the DA uptake carrier might be involved in development of Parkinsons's disease.

Dopamine may play an important role in the etiology of affective disorders (P. Willner, *Brain. Res. Rev.* 1983, 6, 211–224, 225–236 and 237–246; K. P. Bøgesø, *J. Med. Chem.*, 1985, 28, 1817–1828) and DA uptake inhibitors are believed to be effective in treatment of depression (W. Jansen, *Pharmacopsychiat.* 1982, 15, 205–209; H. J. Funke, Pharmacopsychiat., 1986, 19, 120–123).

The stimulant and widely abused drug cocaine is an inhibitor of DA uptake. It has been shown that the potencies of cocaine and cocaine analogs in self-administration studies correlates well with their DA uptake inhibiting potency (M. C. Ritz, *Prog. Neuro-Psychopharmacol. & Boil. Psychiat.*, 1988, 12, 233–239). In squirrel monkeys DA uptake inhibitors show behavioral effects similar to cocaine (S. Rosenzweig-Lipson et al., *Psychopharmacology,* 1992, 107, 186–194). However, in humans, cocaine administered intravenously or by inhalation, has a fast onset and relatively short duration of action which is supposed to be an important part of its stimulating effect. DA uptake inhibitors with different pharmacokinetic properties might not have similar addictive potential and consequently they could be useful in treatment of cocaine addiction and in prevention of relapse (S. Rosenzweig-Lipson et al., *Psychopharmacology,* 1992, 107, 186–194).

It has now surprisingly been found that compounds of the above defined Formula I have high affinity for $D_1$ receptors and that in general they have a higher affinity for $D_1$ receptors than for $D_2$ receptors. Furthermore they have been shown to have high affinity for 5-HT$_2$ receptors and only to induce catalepsy in rats in relatively high doses. Finally, many of the compounds have been found to have dopamine upake inhibiting effect.

The above evidence with respect to effects of substances having a mixed $D_1/D_2$ profile indicates that the present compounds are useful as neuroleptics with effect on psychosis, including positive symptoms of schizophrenia. Additionally, the 5-HT$_2$ receptor antagonistic activity suggests that the compounds have a low risk of extrapyramidal side effects (as also evidenced by the relatively weak cataleptogenic effects). 5-HT$_2$ antagonism and dopamine uptake inhibiting activities indicate that they may also have a beneficial effect on negative symptoms of schizophrenia. So, the present compounds have proven to be very promising neuroleptics with a low incidence of extrapyramidal side effects.

Furthermore, the 5-HT$_2$ receptor antagonistic activity indicates that they may also have an effect on anxiety, depression, sleep disturbances, migraine, and Parkinson's disease (Parkinsonian syndrome) whereas the dopamine uptake inhibition with or without concomitant dopamine antagonistic activity show that they may be effective in the treatment of cocaine abuse. Additionally, the dopamine uptake inhibition indicate that they may be useful in the treatment of Parkinson's disease and depression.

Only trans-isomers of the 1-piperazinoindan derivatives of Formula I are active, cis-isomers being without significant activity.

Accordingly, in a first aspect the present invention relates to trans-isomers of the compounds having the general Formula I as defined above and prodrugs therefore and pharmaceutically acceptable acid addition salts thereof.

The trans-isomers, with respect to the indan ring system, of the invention exist as pairs of optically active isomers and such isomers are within the scope of the present invention. It has so far been found that the $D_1$ (and 5-HT$_2$) antagonistic activity predominantly resides in one of the optical isomers whereas the dopamine uptake inhibiting properties reside in the opposite enantiomer. In certain cases also the piperazine ring of compounds of Formula I contains chiral carbon atoms. The resulting stereoisomers are also within the scope of the invention.

Prodrugs of the present invention are i.a. esters with available hydroxy groups. These esters will decompose properly in order to release the compound of the invention over a desired period of time when administered parenterally as a depot formulation in an appropriate oil, such as coconut oil, e.g. viscoleo®, peanut oil, sesame oil, cotton seed oil, corn oil, soy bean oil, olive oil, etc. or synthetic esters of fatty acids and glycerol or propylenglycol.

The pharmaceutically acceptable acid addition salts of the compounds of the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

Preferred derivatives according to Formula I are those wherein:

X is hydrogen, halogen, lower alkyl or trifluoromethyl;

Y is hydrogen or halogen;

Ar is phenyl, phenyl substituted with halogen, or thienyl;

$R_1$ is hydrogen, lower alkyl, or lower alkyl substituted with hydroxy;

$R_2$ is lower alkyl, or $R_1$ and $R_2$ together with the nitrogen and carbon atoms, respectively, to which they are attached form a piperidino ring fused with the piperazine ring which piperidino ring may optionally be substituted with hydroxy;

$R_3$ is hydrogen or lower alkyl, or $R_2$ and $R_3$ together with the carbon atom to which they are attached form a spirocycloalkyl ring; and $R_4$ is hydrogen or methyl.

Particularly preferred compounds are those wherein:

X is hydrogen, a chloro, bromo, fluoro atom, methyl or trifluoromethyl;

Y is hydrogen;

Ar is phenyl, fluorophenyl or thienyl;

$R_1$ is hydrogen, methyl, 2-propyl, hydroxypropyl or hydroxyethyl;

$R_2$ is $CH_3$, ethyl or 2-propyl and $R_3$ is H ethyl or methyl, or $R_2$ and $R_3$ together with the carbon atom to which they are attached form a spirocyclobutyl or a spirocyclopentyl ring; and $R_4$ is hydrogen.

In a second aspect the present invention relates to a medical preparation comprising at least one derivative of the general Formula I as defined above or a prodrug or a pharmaceutically acceptable acid addition salt thereof together with a pharmaceutically acceptable carrier or diluent. As seen from the above such a pharmaceutical preparation may conveniently comprise a pure enantiomer, a racemate or any other mixture of two enantiomers.

In a further aspect the present invention relates to of a method for the treatment of a disease in the central nervous system, preferably psychosis, schizophrenia (positive as well as negative symptoms), anxiety, depression, sleep disturbances, migraine, Parkinson's disease or cocaine abuse, comprising the step of administering a therapeutically effective dose of a compound having the general Formula I as defined above or a prodrug therefore or a pharmaceutically acceptable acid addition salt thereof together with a suitable carrier or diluent to a patient in need thereof.

The compounds of the Formula I and the pharmaceutically acceptable acid addition salts thereof may be administered by any suitable route, for example orally in the form of tablets, capsules, powders, syrups, etc., or parenterally in the form of solutions for injection.

Suitable pharmaceutical preparations may be prepared by methods well known in the art. Conveniently, the compounds of the invention are administered in unit dosage form containing said compound in an amount of about 0.05–100 mg, preferably about 1–50 mg.

The total daily dose usally ranges from about 0.1 to 500 mg of the active compound of the invention.

The invention moreover relates to a method for the preparation of the novel derivatives of Formula I, which comprises:

a) treating a compound of the Following formula II:

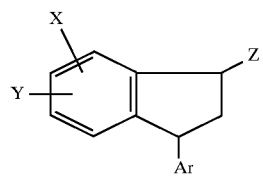

with a piperazine derivative of Formula III:

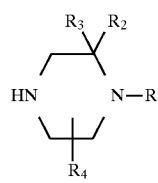

in which formulas X, Y, Ar, $R_1$, $R_2$, $R_3$ and $R_4$ are as defined above, and Z is halogen or $—OSO_2R_6$ wherein $R_6$ is alkyl such as $CH_3$ or aryl such as p-toluyl;

b) treating a compound of the following Formula IV:

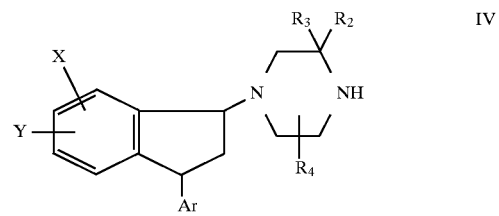

wherein X, Y, Ar, $R_2$, $R_3$ and $R_4$ are as defined above, with a compound of the formula $R_1$-Z wherein $R_1$ and Z are as defined above except that $R_1$ cannot be hydrogen, or with an epoxide of formula

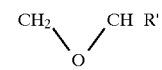

wherein R' is hydrogen, methyl, ethyl, ethenyl, cycloalkyl or cycloalkylalkyl;

c) treating a compound of Formula IV with a compound R"—CHO, wherein R" is hydrogen, $C_1$–$C_3$ alkyl, $C_2$–$C_3$ alkenyl, cycloalkyl or cycloalkylalkyl in the presence of a reducing agent;

d) treating a compound of Formula IV with HCHO/HCOOH to produce derivatives of Formula I wherein $R_1$=methyl (Eschweiler-Clarke methylation);

e) reducing a compound of Formula V:

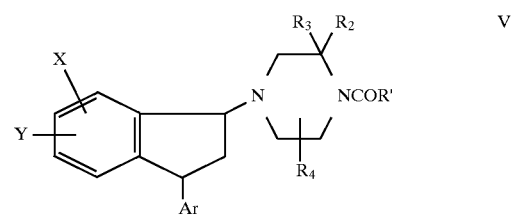

wherein X, Y, Ar, $R_2$, $R_3$ and $R_4$ are as defined above and R' is hydrogen, lower alkoxy, $C_1$–$C_3$ alkyl, $C_2$–$C_3$ alkenyl, cycloalkyl or cycloalkylalkyl;

f) reducing a compound of Formula VI:

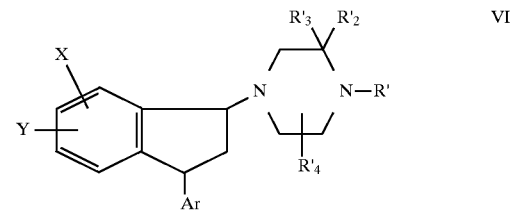

wherein X, Y and Ar are as defined above and one or more of the substituents $R'_1$, $R'_2$, $R'_3$ and $R'_4$ contain one or more ester, ketone or aldehyde groups with a suitable reducing agent to the corresponding compound containing one or more hydroxy groups.

Method a) is preferably carried out in an inert solvent such as acetone or methylisobutylketone using either an excess of the piperazine reactant or by using equimolar amounts of reactants in the presence of an alkali metal carbonate such as potassium carbonate or another alkaline substance at reflux temperatures.

Method b) is preferably carried out in an inert solvent such as ethanol or isobutylketone in the presence of an alkali metal carbonate such as potassium carbonate or another alkaline substance at reflux temperatures.

Method c) is preferably carried out in an inert solvent such as an alcohol (e.g. methanol) or an ether (e.g. tetrahydrofuran) by hydrogenation in the presence of a suitable catalyst such as $PtO_2$ or Pd or by using a borohydride such as $NaCNBH_3$ at a pH of 5–6.

Method d) is preferably carried out with an excess of formaldehyde in formic acid at reflux temperatures.

Method e) is preferably carried out in an inert solvent such as diethylether or tetrahydrofurane using a suitable reducing agent such as $LiAlH_4$.

Method f) is preferably carried out in an inert solvent such as diethylether or tetrahydrofurane using a suitable reducing agent such as $LiAlH_4$ or a borohydride e.g. $NaBH_4$.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or with an excess of the acid in an aqueous immiscible solvent, such as ethyl ether or chloroform, with the desired salt separating directly. Of course, these salts may also be prepared by the classical method of double decomposition of appropriate salts.

The separation of the compounds of Formula I in the individual optical isomers may be performed by methods well known in the art.

The compounds of Formula II may be prepared from the corresponding 2,3-dihydro-inden-1-ones by a method analogously with the method described in U.S. Pat. No. 4,443,448, U.S. Pat. No. 4,684,650, and J.Med.Chem. 1983, 26, 935–947. The indanones were either prepared by cyclization of the corresponding diphenylpropionic acids or more conveniently as described for similar compounds in U.S. Pat. No. 4,873,344 and in J.Org.Chem. 1990, 5, 4822 from properly substituted 1-amino-3-cyano-1-inden-2-carboxylic acid esters which in turn also may be prepared as described in U.S. Pat. No. 4,873,344.

Some piperazine derivatives III are commercially available (2-methylpiperazine, 2,5-dimethylpiperazine and 2,6-dimethylpiperazine) while other piperazines were prepared by methods established in the literature: 2-isopropylpiperazine (Beilstein 3 & 4 erganzungswerk, 23, 430 and references cited there); octahydropyrido[1,2-a]pyrazine, IIIa (Peck R. L. and Day A. R.; J. Heterocycl. Chem. 1969, 6, 181–185).

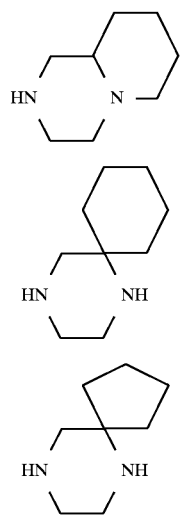

1,4-Diazaspiro[5.5]undecane, IIIb and 6,9-diazaspiro[4.5]decane, IIIc, have been reported in the literature (Granger R. et al; Trav. Soc. Pharm. Montpellier 1965, 25, 313–317) but were like 5,8-diazaspiro[3.5]nonane, IIId, prepared by the same procedure as described for 2,2-dimethylpiperazine and 2,2-diethylpiperazine below.

Obviously, the compounds of Formula IV may be prepared by method a). The compounds of Formulas V and VI may be prepared from compounds of Formula IV by methods well known in the art.

In the following the invention is further illustrated by examples which in no way may be construed as limiting for the invention.

EXAMPLES

Example 1

2,2-Dimethylpiperazine.

To a mixture of isoburtyaldehyde (790 g, 10.95 mol) and dioxane (39.5 g, 0.45 mol) in dry ether (4 L) was added 11 mL of bromine at room temperature. The mixture was cooled to 5° C. and further 509 mL (1588 g, 9.93 mol) bromine was added at 5°–10° C. The reaction mixture was poured into 4 L of ice water where-upon sodium carbonate (600 g) was gradually added with stirring. The organic phase was separated, dried ($MgSO_4$) and distilled to yield 1150 g (69.6%) of 2-bromo-isoburtyaldehyde, bp 70°–77° C. (170 mm Hg).

2-Bromo-isoburtyaldehyde (1070 g, 7.09 mol) was added with vigorous stirring to a mixture of ethylenediamine (2.2 kg, 36.6 mol) and toluene at 5°–10° C. The reaction mixture was stirred at room temperature for 1 h and was then refluxed for 30 min. The toluene phase was separated and the lower phase was extracted twice with 500 mL of toluene. The toluene phase was concentrated in vacuo and the residue was distilled to give 450 g (56.6%) of crude 2,2-dimethyl-1,2,5,6-tetrahydro-pyrazine, bp 80°–120° C. (170 mm Hg).

To a solution of the crude 2,2-dimethyl-1,2,5,6-tetrahydropyrazine (450 g) in 1 L ethanol was added 5% Pd/C (20 g) and the reaction mixture was hydrogenated in a Parr apparatus at 3.5 ato until the consumption of hydrogen (2.2 mol) stopped. After filtration the reaction mixture was distilled at atmospheric pressure. The fraction boiling at 140°–180° C. was collected and redistilled to yield 159 g (19.8% from 2-bromo-isoburtyaldehyde) of 2,2-dimethylpiperazine, bp 150°–170° C. (760 mm Hg). $^1$H NMR (250 MHz, $CDCl_3$) δ1.12 (s, 6H), 1.33 (br s, 2H, NH), 2.60 (s, 2H), 2.76 (t, 2H), 2.85 (t, 2H).

The product solidified upon standing (mp below 35° C.).

2,2-Diethylpiperazine and the piperazine derivatives IIIa–d were prepared in a similar manner.

Example 2

(±)-Trans-4-[6-chloro-3-(4-fluorophenyl)-2,3-dihydro-1H-inden-1-yl]-2,2-dimethylpiperazine, hemifumarate, 1.

A mixture of 1,6-dichloro-3-(4-fluorophenyl)-2,3-dihydro-1H-indene (28 g, 0.1 mol), 2,2-dimethylpiperazine (15 g, 0.13 mol) and potassium carbonate (30 g) in acetone (250 mL) was refluxed for 18 h. The reaction mixture was evaporated in vacuo and treated with water and ether. The ether phase was separated and extracted with 1M methane sulfonic acid. The base was liberated with 10M sodium hydroxide, extracted with ether and dried ($MgSO_4$). After filtration and evaporation in vacuo the residue was dissolved in acetone and treated with fumaric acid. The fumarate salt was filtered to give 27 g of 1 as the hemifumarate salt, mp 240°–241° C. A sample recrystallized from ethanol had mp 242°–244° C. Isomeric purity (TLC): 95% trans isomer (racemate).

CHN calcd.: 66.25%; 6.30%; 6.72%. CHN found: 66.05%; 6.49%; 6.44%.

Example 3

(±)-Trans-4-[6-chloro-3-(4-fluorophenyl)-2,3-dihydro-1H-inden-1 -yl]-1,2,2-trimethylpiperazine, maleate, 2.

A mixture of the hemifumarate of 1 (23 g, 0.055 mol, see Example 1), 37% formaldehyde (100 mL) and formic acid (100 mL). The clear solution was heated on a steam bath for 2 h and was then evaporated in vacuo. The residue was converted to the base in a conventional manner. The base was dissolved in ethyl acetate and treated with maleic acid. The maleate was recrystallized from ethyl acetate to give 13.5 g (50%) of 2, maleate, mp 143°–146° C. Isomeric purity (TLC): >98% trans isomer (racemate).

CHN calcd.: 63.85%; 6.20%; 5.73%. CHN found: 63.77%; 6.27%; 5.65%.

The methods described in Example 2 and Example 3 (N-methyl derivatives) were used for the- preparation of the following compounds:

(±)-Trans-4-[3-phenyl-2,3-dihydro-1H-inden-1-yl]-1,2,2-trimethyl-piperazine, dimaleate; mp 162°–165° C. Compd. 3.

(±)-Trans-2,2-dimethyl-4-[6-methyl-3-(4-fluorophenyl)-2,3-dihydro-1H-inden-1-yl]piperazine; mp 108°–110° C. Compd. 4.

(±)-Trans-4-[6-methyl-3-(4-fluorophenyl)-2,3-dihydro-1H-inden-1-yl]-1,2,2-trimethylpiperazine; mp 119°–121° C. Compd. 5.

(±)-Trans-2,2-dimethyl-4-[6-trifluoromethyl-3-(4-fluorophenyl)-2,3-dihydro-1H-inden-1-yl]piperazine; mp 94°–95° C. Compd. 6.

(±)-Trans-4-[6-trifluoromethyl-3-(4-fluorophenyl)-2,3-dihydro-1H-inden-1-yl]-1,2,2-trimethylpiperazine; mp 112°–114° C. Compd. 7.

(±)-Trans-4-[6-bromo-3-(4-fluorophenyl)-2,3-dihydro-1H-inden-1-yl]-1,2,2-trimethylpiperazine, 1.5 fumarate; mp 142°–145° C. Compd. 8.

(±)-Trans-4-[5,6-dichloro-3-(4-fluorophenyl)-2,3-dihydro-1H-inden-1-yl]-1,2,2-trimethylpiperazine, 1.5 fumarate; mp 182°–184° C. Compd. 9.

(±)-Trans-4-[6-chloro-3-phenyl-2,3-dihydro-1H-inden-1-yl] -1,2,2-trimethylpiperazine, 1.5 maleate; mp 170°–171° C. Compd. 10.

(±)-Trans-4-[6-chloro-3-(2-fluorophenyl)-2,3-dihydro-1H-inden-1-yl]-1,2,2-trimethylpiperazine, dimaleate; mp 154°–156° C. Compd. 11.

(±)-Trans-4-[6-chloro-3-(3-fluorophenyl)-2,3-dihydro-1H-inden-1-yl]-1,2,2-trimethylpiperazine, dimaleate; mp 140°–142° C. Compd. 12.

(±)-Trans-4-[6-chloro-3-(3-thienyl)-2,3-dihydro-1H-inden-1-yl]-2,2-dimethylpiperazine, dimaleate; mp 163°–165° C. Compd. 13.

(±)-Trans-4-[6-chloro-3-(3-thienyl)-2,3-dihydro-1H-inden-1-yl]-1,2,2-trimethylpiperazine, dihydrochloride; mp 173°–176° C. Compd. 14.

(±)-Trans-4-[4-chloro-3-(4-fluorophenyl)-2,3-dihydro-1H-inden-1-yl]-1,2,2-trimethylpiperazine, dioxalate; mp 120°–125° C. Compd. 15.

(±)-Trans-4-[5-chloro-3-(4-fluorophenyl)-2,3-dihydro-1H-inden-1-yl]-1,2,2-trimethylpiperazine; mp 126°–128° C. Compd. 16.

(±)-Trans-4-[7-chloro-3-(4-fluorophenyl)-2,3-dihydro-1H-inden-1-yl]-1,2,2-trimethylpiperazine, 1.3 oxalate; mp 153°–155° C. Compd. 17.

(±)-Trans-4-[6-chloro-3-(4-fluorophenyl)-2,3-dihydro-1H-inden-1-yl]-1,2-dimethylpiperazine, dimaleate; mp 181°–183° C. Compd. 18.

Trans-4-[6-chloro-3-(4-fluorophenyl)-2,3-dihydro-1H-inden-1-yl]-2-(2-propyl)piperazine, dimaleate; mp 135°–137° C. Pair 1 of diastereomeric trans isomers. Compd. 19.

Trans-4-[6-chloro-3-(4-fluorophenyl)-2,3-dihydro-1H-inden-1-yl]-2-(2-propyl)piperazine, maleate; mp 156°–159° C. Pair 2 of diastereomeric trans isomers. Compd. 20.

Trans-4-[6-chloro-3-(4-fluorophenyl)-2,3-dihydro-1H-inden-1-yl]-1-methyl-2-(2-propyl)piperazine, dimaleate; mp 119°–122° C. Pair 1 of diastereomeric trans isomers. Compd. 21.

Trans-4-[6-chloro-3-(4-fluorophenyl)-2,3-dihydro-1H-inden-1-yl]-1-methyl-2-(2-propyl)piperazine, dimaleate; mp 160°–162° C. Pair 2 of diastereomeric trans isomers. Compd. 22.

(±)-Trans-4-[6-chloro-3-(4-fluorophenyl)-2,3-dihydro-1H-inden-1-yl]-2,2-diethylpiperazine, fumarate; mp 231°–233° C. Compd. 23.

(±)-Trans-4-[6-chloro-3-(4-fluorophenyl)-2,3-dihydro-1H-inden-1-yl]-2,2-diethyl-1-methylpiperazine, oxalate; mp 144°–146° C. Compd. 24.

(±)-Trans-4-[6-chloro-3-(4-fluorophenyl)-2,3-dihydro-1H-inden-1-yl]-(1-trans-2,5-trimethyl)piperazine, maleate; mp 166°–169° C. Compd. 25.

(±)-Trans-4-[6-chloro-3-(4-fluorophenyl)-2,3-dihydro-1H-inden-1-yl]-(1-cis-2,6-trimethyl)piperazine, dioxalate; mp 158°–160° C. Compd. 26.

(±)-Trans-4-[6-trifluoromethyl-3-(4-fluorophenyl)-2,3-dihydro-1H-inden-1-yl]-cis-2,6-dimethylpiperazine, dihydrochloride; mp 255°–260° C. Compd. 27.

(±)-Trans-8-[6-chloro-3-(4-fluorophenyl)-2,3-dihydro-1H-inden-1-yl]-5-methyl-5,8-diazaspiro[3.5]nonane, dihydrochloride; mp 188°–190° C. Compd. 28.

(±)-Trans-9-[6-chloro-3-(4-fluorophenyl)-2,3-dihydro-1H-inden- 1-yl]-6-methyl-6,9-diazaspiro[4.5]decane, fumarate; mp 144°–147° C. Compd. 29.

(±)-Trans-9-[6-chloro-3-(3-thienyl)-2,3-dihydro-1H-inden-1-yl]-6-methyl-6,9-diazaspiro[4.5]decane, dihydrochloride; mp 182°–184° C. Compd. 30.

(±)-Trans-4-[6-chloro-3-(4-fluorophenyl)-2,3-dihydro-1H-inden-1-yl]-1,4-diazaspiro[5.5]undecan, fumarate; mp 241°–243° C. Compd. 31.

(±)-Trans-4-[6-chloro-3-(4-fluorophenyl)-2,3-dihydro-1H-inden-1-yl]-1-methyl-1,4-diazaspiro[5.5]undecan, dihydrochloride; mp 205°–207° C. Compd. 32.

2-[6-fluoro-3-(4-fluorophenyl)-2,3-dihydro-1H-inden-1-yl]-octahydropyrido[1,2-a]-pyrazine, dihydrochloride; mp 225°–227° C. 1:1 mixture of cis and trans isomers. Compd. 33.

(±)-Trans-2-[6-chloro-3-(4-fluorophenyl)-2,3-dihydro-1H-inden-1-yl]-octahydropyrido[1,2-a]pyrazine, dimaleate; mp 172°–174° C. Compd. 34.

2-[6-fluoro-3-(4-fluorophenyl)-2,3-dihydro-1H-inden-1-yl]-octahydropyrido[1,2-a]-pyrazine-8-ol, dihydrochloride; mp 223°–225° C. 1:1 mixture of cis and trans isomers. Compd. 35.

(±)-Trans-4-[7-fluoro-3-(4-fluoro phenyl)-2,3-dihydro-1H-inden-1-yl]-1,2,2-trimethyl piperazine, oxalate; mp 133°–135° C. Compd. 36.

(±)-Trans-4-[3-(4-fluorophenyl)-2,3-dihydro-1H-inden-1-yl]-1,2,2-trimethylpiperazine, dimaleate; mp 135°–137° C. Compd. 37.

(±)-Trans-4-[6-fluoro-3-(4-fluoro phenyl)-2,3-dihydro-1H-inden-1-yl]-1,2,2-trimethyl piperazine, dimaleate; mp 154°–156° C. Compd. 38.

Example 4

(±)-Trans-4-[6-chloro-3-(4-fluorophenyl)-2,3-dihydro-1H-inden-1-yl]-2,2-dimethyl-1-piperazinepropanol, maleate, 39.

A mixture of 1 (base, 6 g, 0.017 mol), 3-chloro-1-propanol (1.9 g, 0.020 mol) and potassium carbonate (3 g, 0.021 mol) in ethanol (250 mL) was refluxed overnight. The reaction mixture was worked-up as described in Example 2 to give 6 g of crude base. The base was converted to the maleate salt in ethyl acetate and was recrystallized twice from acetone-ether to give 2.5 g 39, maleate, mp 177°–178° C.
Isomeric purity (TLC): 92% trans isomer (racemate).
CHN calcd.: 63.08%; 6.44%; 5.26%.
CHN found: 63.28%; 6.15%; 5.62%.

The method described in Example 4 were used for the preparation of the following compounds:
(±)-Trans-4-[6-chloro-3-(4-fluorophenyl)-2,3-dihydro-1H-inden-1-yl]-2,2-dimethyl-1-(2-propyl)piperazine, dioxalate; mp 157°–159° C. Compd. 40.
(±)-Trans-4-[6-chloro-3-(4-fluorophenyl)-2,3-dihydro-1H-inden-1-yl]-2-methyl-1-(2-propyl)piperazine, dimaleate; mp 89°–92° C. Compd. 41.
(±)-Trans-9-[6-chloro-3-(4-fluorophenyl)-2,3-dihydro-1H-inden-1-yl]-6-(2-propyl)-6,9-diazaspiro[4.5]decane, dihydrochloride; mp 237°–238° C. Compd. 42.

Example 5

(±)-Trans-4-[6-chloro-3-(4-fluorophenyl)-2,3-dihydro-1H-inden-1-yl]-2,2-dimethyl-1-piperazineethanol, 43.

A mixture of 1 (base, 5.4 g, 0.015 mol), ethyl bromoacetate (3.3 g, 0.020 mol) and potassium carbonate (3 g, 0.021 mol) in methyl isobutylketone was refluxed for 4 h. The reaction mixture was evaporated in vacuo and treated with ether and water. The ether phase was dried (MgSO$_4$) and evaporated to give 7 g of crude ester. The ester was dissolved in dry ether, LiAlH$_4$ (2 g) was added and the mixture was refluxed for 3 h. The excess LiAlH$_4$ was destroyed with water, the organic phase was decanted, and the product was extracted from the ether phase with 1N methane sulfonic acid. The base was liberated with 10N NaOH, extracted with ether, dried and evaporated in vacuo. The base crystallized from petroleum ether to yield 1.1 g, mp 79°–81° C. Isomeric purity (TLC): 99% trans isomer (racemate).
CHN calcd.: 68.55%; 7.02%; 6.95%.
CHN found: 68.77%; 7.32%; 6.78%.

The method described in Example 5 were used for the preparation of the following compounds:
(±)-Trans-9-[6-chloro-3-(4-fluorophenyl)-2,3-dihydro-1H-inden-1-yl]-6-(2-hydroxyethyl)-6,9-diazaspiro[4.5]decane, dihydrochloride; mp 167°–169° C. Compd. 44.

(±)-Trans-4-[6-chloro-3-(3-thienyl)-2,3-dihydro-1H-inden-1-yl]-2,2-dimethyl-1-piperazineethanol, dihydrochloride; mp 213°–215° C. Compd. 45.

Example 6

(+) and (−) Trans-4-[6-chloro-3-(4-fluorophenyl)-2,3-dihydro-1H-inden-1-yl]-1,2,2-trimethylpiperazine, maleate, (+)-2 and (−)-2.

To a solution of 2 (base, 70 g, 0.187 mol) in 1 L of ethyl acetate was added (+)-O,O'-dibenzoyl-D-tartaric acid hydrate ((+)-DBT, 70.6 g, 0.189 mol). The clear solution was left at room temperature overnight. The crude (+)-DBT salt was filtered, dried (yield 53 g) and recrystallized from ethyl acetate-methanol. The (+)-DBT salt (mp 123°–128° C.) was converted to the base which was dissolved in acetone and converted to the hydrochloride. Yield: 13 g (−)-2, dihydrochloride, mp 201°–202° C.; [α]$^{22}_D$ −23.4° (c 0.5, MeOH).

The first filtrate from the (+)-DBT salt was evaporated in vacuo and converted to the base (38 g), which was dissolved in ethyl acetate and treated with (−)-DBT hydrate (38.3 g) to give the (−)-DBT salt. This was converted to the hydrochloride as described for the (−)-enantiomer. Yield: 14.8 g of (+)-2, dihydrochloride, mp 206°–208° C.; [α]$^{22}_D$ +24.5° (c 0.5, MeOH).
CHN calcd.: 59.26%; 6.34%; 6.28%.
CHN found: 59.33%; 6.64%; 6.46% ((−)-2).
CHN found: 59.05%; 6.47%; 6.04% ((+)-2).

Compound 29, 37, 40 and 44 were separated into their enantiomers using a similar procedure as described in Example 6:
(−)-Trans-9-[6-chloro-3-(4-fluorophenyl)-2,3-dihydro-1H-inden-1-yl]-6-methyl-6,9-diazaspiro[4.5]decane, dihydrochloride; mp 204°–206° C.; [α]$^{22}_D$ −13.8° (c 1, DMF). Compd. (−)-29.
(+)-Trans-9-[6-chloro-3-(4-fluorophenyl)-2,3-dihydro-1H-inden-1-yl]-6-methyl-6,9-diazaspiro[4.5]decane, dihydrochloride; mp 205°–207° C.; [α]$^{22}_D$ +10.5° (c 1, DMF). Compd. (+)-29.
(−)-Trans-4-[3-(4-fluorophenyl)-2,3-dihydro-1H-inden-1-yl]-1,2,2-trimethyipiperazine, dimaleate; mp 197°–199° C.; [α]$^{22}_D$ −2.7° (c 0.5, CH$_3$OH). Compd. (−)-37.
(+)-Trans-4-[3-(4-fluorophenyl)-2,3-dihydro-1H-inden-1-yl]-1,2,2-trimethylpiperazine, dimaleate; mp 198°–199° C.; [α]$^{22}_D$ −2.5° (c 0.5, CH$_3$OH). Compd. (+)-37.
(−)-Trans-4-[6-chloro-3-(4-fluorophenyl)-2,3-dihydro-1H-inden-1-yl]-2,2-dimethyl-1-(2-propyl)-piperazine, dioxalate; mp 169°–171° C. [α]$^{22}_D$ −18.4° (c 1, MeOH). Compd. (−)-40
(+)-Trans-4-[6-chloro-3-(4-fluorophenyl)-2,3-dihydro-1H-inden-1-yl]-2,2-dimethyl-1-(2-propyl)-piperazine, dioxalate; mp 171°–172° C. [α]$^{22}_D$ +18.2° (c 1, MeOH). Compd. (+)-40.
(−)-Trans-9-[6-chloro-3-(4-fluorophenyl)-2,3-dihydro-1H-inden-1-yl]-6-(2-hydroxyethyl)-6,9-diazaspiro[4.5]decane, dihydrobromide; mp 197°–199° C. [α]$^{22}_D$ −10.2° (c 1, MeOH). Compd. (−)-44.
(+)-Trans-9-[6-chloro-3-(4-fluorophenyl)-2,3-dihydro-1H-inden-1-yl]-6-(2-hydroxyethyl)-6,9-diazaspiro[4.5]decane, dihydrobromide; mp 206°–208° C. [α]$^{22}_D$ +10.7° (c 1, MeOH). Compd. (+)-44.

PHARMACOLOGY

The present compounds were tested in the following well known and reliable pharmacological test methods.
Receptor binding studies.
DA D$_1$ receptors. Inhibition of $^3$H-SCH 23390 binding to DA D$_1$ receptors in rat striatal membranes was determined as described by Hyttel, J. and Arnt, J. *J. Neural. Transm.* 1987, 68, 171.

DA $D_2$ receptors. Inhibition of $^3$H-spiperone binding to DA $D_2$ receptors in rat striatal membranes was determined as described by Hyttel, J. *Acta. Pharmacol. Toxicol.* 1986, 59, 387.

5-HT$_2$ receptors. Inhibition of $^3$H-ketanserin binding to 5-HT$_2$ receptors in membranes from rat cortex was determined as described by Hyttel, J. *Acta. Pharmacol. Toxicol.* 1987, 61, 126.

The affinity to $D_1$, $D_2$ and 5-HT$_2$ receptors of the compounds described in the examples above are shown in the following Table 1. The reference compounds tefludazine, irindalone and clozapine were included in the tests for comparizon purposes.

TABLE 1

Receptor Binding; IC$_{50}$ values in nM

| Compound | $D_1$ $^3$H-SCH | $D_2$ $^3$H-Spi | 5-HT$_2$ $^3$H-Ket |
|---|---|---|---|
| 1 | 2.1 | 7.3 | 3.2 |
| 2 | 1.3 | 25 | 2.1 |
| −2 | 0.68 | 5.0 | 1.1 |
| +2 | 620 | >1000 | 2000 |
| 3 | 13 | 140 | 21 |
| 4 | 5.9 | 5.6 | 1.5 |
| 5 | 2.1 | 4.8 | 3.4 |
| 6 | 2.8 | 5.2 | |
| 7 | 1.5 | 5.7 | 4.5 |
| 8 | 1.8 | 8.6 | 3.0 |
| 9 | 18 | 44 | 5.9 |
| 10 | 1.6 | 20 | 3.2 |
| 11 | 4.4 | 36 | 21 |
| 12 | 9.6 | 280 | 26 |
| 13 | 1.4 | 8.2 | 1.0 |
| 14 | 0.76 | 6.1 | 1.7 |
| 15 | 45 | 55 | 29 |
| 16 | 37 | 340 | 9.3 |
| 17 | 32 | 1200 | 31 |
| 18 | 2.4 | 12 | |
| 19 | 2.2 | 38 | 5.6 |
| 20 | 6.0 | 130 | 8.8 |
| 21 | 3.2 | 36 | |
| 22 | 43 | 400 | |
| 23 | 4.7 | 36 | 11 |
| 24 | 8.8 | 38 | |
| 25 | 19 | 41 | 3.4 |
| 26 | 13 | 120 | 3.3 |
| 27 | 50 | 33 | |
| 28 | 0.89 | 6.3 | 3.0 |
| 29 | 0.85 | 10 | 5.2 |
| −29 | 0.96 | 4.5 | 4.0 |
| +29 | 6.6 | 20 | 13 |
| 30 | 1.8 | 5.0 | |
| 31 | 6.4 | 75 | 25 |
| 32 | 6.0 | 24 | |
| 33 | 5.8 | 320 | 28 |
| 34 | 2.1 | 11 | |
| 35 | 30 | 1100 | |
| 36 | 3.8 | 74 | 9.8 |
| 37 | 3.0 | 29 | 5.1 |
| −37 | 2.5 | 12 | 2.9 |
| +37 | 250 | 4900 | 650 |
| 38 | 0.88 | 11 | 3.6 |
| 39 | 1.8 | 9.8 | 3.0 |
| 40 | 0.82 | 5.0 | 4.1 |
| −40 | 0.66 | 3.1 | 2.5 |
| +40 | 52 | | |
| 41 | 1.6 | 17 | |
| 42 | 1.3 | 8.8 | |
| 43 | 1.0 | 3.0 | |
| 44 | 1.9 | 13 | 6.0 |
| −44 | 1.0 | 5.0 | 2.5 |
| +44 | 51 | | |
| 45 | 0.82 | 2.8 | |

TABLE 1-continued

Receptor Binding; IC$_{50}$ values in nM

| Compound | $D_1$ $^3$H-SCH | $D_2$ $^3$H-Spi | 5-HT$_2$ $^3$H-Ket |
|---|---|---|---|
| Tefludazine | 23 | 10 | 4.6 |
| Irindalone | 890 | 400 | 3.4 |
| Clozapine | 130 | 330 | 7.8 |

The results in the Table show that in general the compounds have very high affinity to $D_1$ receptors (IC$_{50}$ values in the low nanomolar range). In most cases the affinity to $D_2$ receptors is considerably lower. The $D_2/D_1$ ratio is therefore higher and in many cases considerably higher, than for the reference compound clozapine. Furthermore, it appears that the compounds have affinity for the 5-HT$_2$ receptor and data with respect to resolved compounds show that the affinities predominantly reside in one enantiomer.

DA uptake inhibition.

Inhibition of DA Uptake in Vitro was determined as described by K. P. Bøgesø, *J. Med. Chem.* 1983, 26, 935–947.

For racemic compounds the IC$_{50}$ values for inhibition of DA uptake were generally <1 μmol. Some compounds were active in the low nanomolar range. Thus, IC$_{50}$ values were 16 nM (compd. (+)-2), 15 nM (compd. 10), 36 nM (compd. 37) and 9 nM (compd. 38; the corresponding prior art compound with an unsubstituted piperazine ring had an IC$_{50}$ value of 180 nM, see K. P. Bøgesø, *J. Med. Chem.* 1983, 26, 935–947). In resolved compounds the dopamine uptake inhibition was seen to reside mainly in the opposite enantiomer of the above binding affinities.

PHARMACOLOGY IN VIVO

Antagonism of SK&F 38393-induced circling behavior in rats with unilateral 6-OHDA lesions.

This test is a test for the DA $D_1$ receptor antagonistic effect in vivo.

The experiments were performed as described by Arnt, J. and Hyttel, J. *J. Neural. Transm.* 1986, 67, 225–240. The experiments were done 2–9 months after lesioning when stable contralateral circling response to 2,3,4,5-tetrahydro-7,8-dihydroxy-1-phenyl-1H-3-benzazepine, hydrochloride (SK&F 38393) (4.3 μmol/kg=1.4 mg/kg) were obtained. The test compounds were injected 2 h before administration of SK&F 38393. Antagonistic effect were calculated as percent inhibition of control responses for each rat. Four to eight animals were used per dose.

Cataleptogenic effect in rats.

Catalepsy was measured every hour 1–6 h after test drug administration on a vertical wire grid and defined as being present after at least 15-simmobility. The maximum effect between 1–6 h after administration was reported. A total of 8–12 animals were used per dose.

Most of the compounds were very active as $D_1$ antagonists in vivo (antagonism of SK&F 38393-induced circling behavior). The ED$_{50}$'s were for many compounds in the range 0.2–2 μmol/kg. For example, the ED$_{50}$ for compound 38 was 0.50 μmol/kg. For many compounds catalepsy was absent or only induced in doses much higher than the doses needed to antagonize the SK&F 38393-induced circling behavior. The ED$_{50}$'s in the catalepsy test were typically in the range from 5 to 90 μmol/kg. For compound 38 the ED$_{50}$ were >68 μmol/kg.

A weak or absent effect in the catalepsy test indicate a low potential for inducing motoric (extrapyramidal) side-effects in man.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5 milligrams of Compound 38 calculated as the free base:

| | |
|---|---|
| Compn. 38 | 2 mg |
| Lactose | 18 mg |
| Potato starch | 27 mg |
| Sucrose | 58 mg |
| Sorbitol | 3 mg |
| Talcum | 5 mg |
| Gelatine | 2 mg |
| Povidone | 1 mg |
| Magnesium stearate | 0.5 mg |

2) Tablets containing 50 milligrams of Compound 28 calculated as the free base:

| | |
|---|---|
| Compn. 28 | 5 mg |
| Lactose | 16 mg |
| Potato starch | 45 mg |
| Sucrose | 106 mg |
| Sorbitol | 6 mg |
| Talcum | 9 mg |
| Gelatine | 4 mg |
| Povidone | 3 mg |
| Magnesium stearate | 0.6 mg |

3) Syrup containing per milliliter:

| | |
|---|---|
| Compn. 2 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

4) Solution for injection containing per milliliter:

| | |
|---|---|
| Compn. 14 | 50 mg |
| Acetic acid | 17.9 mg |
| Sterile water | ad 1 ml |

5) Solution for injection containing per milliliter:

| | |
|---|---|
| Comp. 29 | 10 mg |
| Sorbitol | 42.9 mg |
| Acetic acid | 0.63 mg |
| Sodium hydroxide | 22 mg |
| Sterile water | ad 1 ml |

We claim:

1. Trans isomers of 1-piperazino-1,2-dihydroindene compounds having the Formula I:

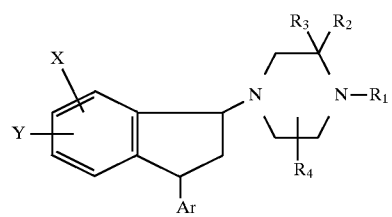

wherein X and Y are independently selected from the group consisting of hydrogen, halogen, trifluoromethyl, lower alkyl, and nitro;

Ar is a phenyl group, a phenyl group substituted with one or more substituents selected from the group consisting of halogen and lower alkyl, or Ar is a thienyl group or a thienyl group substituted with halogen or lower alkyl;

$R_1$ is hydrogen or lower alkyl optionally substituted with one or two hydroxy groups;

$R_2$ is methyl;

$R_3$ is hydrogen or methyl; or $R_2$ and $R_3$ together with the carbon atom to which they are attached form a 3 to 5-membered carbocyclic ring which is spiro-fused to the piperazine ring; and $R_4$ is hydrogen;

or pharmaceutically acceptable acid addition salts thereof.

2. A compound according to claim 1, wherein

Y is hydrogen or halogen;

Ar is phenyl, phenyl substituted with halogen, or thienyl;

$R_1$ is hydrogen, lower alkyl, or lower alkyl substituted with hydroxy;

$R_2$ is methyl;

$R_3$ is hydrogen or methyl; or $R_2$ and $R_3$ together with the carbon atom to which they are attached form a $C_{4-5}$ spirocycloalkyl ring; and $R_4$ is hydrogen.

3. A compound according to claim 1, wherein,

X is hydrogen, a chloro, bromo or fluoro atom, methyl or trifluoromethyl;

Y is hydrogen;

Ar is phenyl, fluorophenyl or thienyl;

$R_1$ is hydrogen, methyl, 2-propyl, hydroxypropyl, or hydroxyethyl;

$R_2$ is $CH_3$ and $R_3$ is H, or methyl, or $R_2$ and $R_3$ together with the carbon atom to which they are attached form a spirocyclobutyl or a spirocyclopentyl ring; and $R_4$ is hydrogen.

4. A pharmaceutical preparation, comprising at least one compound according to claim 1 together with a pharmaceutically acceptable carrier or diluent.

5. A pharmaceutical preparation according to claim 4, wherein the compound according to claim 1 is present as a pure enantiomer, a racemate or any other mixture of the two enantiomers.

6. A method for treating schizophrenia symptoms, anxiety, or depression, comprising the step of administering a therapeutically effective amount of a compound of claim 1 with a suitable carrier or diluent.

7. A compound according to claim 1, selected from the group consisting of (±)-Trans4-[6-chloro-3-(4-fluorophenyl)-2,3-dihydro-1H-inden-1-yl]-2,2-dimethylpiperazine;

(±)-Trans4-[6-chloro-3-phenyl-2,3-dihydro-1H-inden-1-yl]-1,2,2-trimethylpiperazine;

(±)-Trans-4-[6-chloro-3-(3-thienyl)-2,3-dihydro-1H-inden-1-yl]-2,2-dimethylpiperazine; and (±)-Trans-4-[3-(4-fluorophenyl)-2,3-dihydro-1H-inden-1-yl]-1,2,2-trimethylpiperazine.

* * * * *